United States Patent [19]

Patel et al.

[11] Patent Number: 4,486,445
[45] Date of Patent: Dec. 4, 1984

[54] JUSTICIDIN INSECTICIDAL AND ANTIVIRAL COMPOUNDS

[75] Inventors: Narayan G. Patel; Chia-Lin J. Wang, both of Wilmington, Del.

[73] Assignee: E. I. Du Pont de Nemours and Company, Wilmington, Del.

[21] Appl. No.: 457,372

[22] Filed: Jan. 12, 1983

[51] Int. Cl.$^3$ .................... C07D 407/02; A61K 31/34
[52] U.S. Cl. ..................................... 424/279; 549/299
[58] Field of Search .......................... 549/299; 424/279

[56] References Cited

U.S. PATENT DOCUMENTS 3,704,247  11/1972  Munakata et al. .................. 549/299

FOREIGN PATENT DOCUMENTS 140268  9/1981  Japan ................................. 549/299

OTHER PUBLICATIONS

Meyers et al., C.A. 95:115107u.
Govindachari et al., C.A. 68:114464.
Munakata et al., C.A. 68:95728j.
Ohta et al., *Agr. Biol. Chem.*, 33: 610–614, (1969).
Ohta et al., *Tetrahedron Letters* No. 12: 923–925, (1970).
Chen, *Proc. 5th Asian Congress Pharm. Sci. Fer.,* (1974), pp. 79–86.
Ghosal, et al., *Chemistry and Industry,* (1979), pp. 854–855.
Markannen, et al., *Drugs Exptl. Clin. Res.* VII(6): (1981), pp. 711–718.
Munakata et al., *Tetrahedron Letters* No. 47, pp. 4167–4170, (1965).
Munakata et al., *Tetrahedron Letters* No. 39, pp. 3821–3825, (1967).
Horii et al., *Chem. Pharm. Bull.* 19: 535–537, (1971).
Horii et al., *Chem. Comm.,* 1968, pp. 653–655.
Wada et al., *Tetrahedron Letters* No. 13, pp. 2017–2019, (1970).
Ziegler et al., *J. Org. Chem.* 43: pp. 985–991, (1978).
Gonzalez et al., *Tetrahedron.* 34: pp. 1011–1013, (1978).
Olaniyi, *Planta Med.* 44: pp. 154–156, (1982).

*Primary Examiner*—Jane T. Fan
*Attorney, Agent, or Firm*—Scott G. Hallquist

[57] ABSTRACT

A natural lignan of the 1-aryl-2-napthoic acid type and related compounds are disclosed. The compounds correspond to the formula

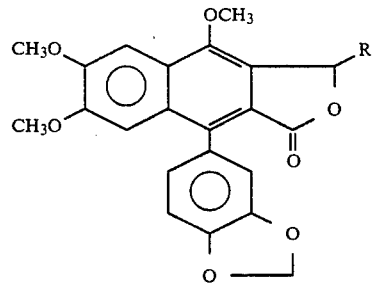

and exhibit both insecticidal and antiviral activity.

30 Claims, No Drawings

JUSTICIDIN INSECTICIDAL AND ANTIVIRAL COMPOUNDS

BACKGROUND OF THE INVENTION

This invention relates to certain insecticidal or antiviral compounds classified as justicidins, to insecticidal and antiviral compositions containing these compounds, and to methods of using the compositions to kill insects or to treat viral infection in mammals.

Natural 1-aryl-2- or -3-napthoic acid lignan compounds have previously been isolated from various sources. Some of these compounds have been associated with bioactive properties.

Ohta, et al., Agr. Biol. Chem. 33:610–614 (1969), describe the isolation of justicidins A and B, and report that these compounds are active piscicidal components of *Justicia Hayatai var. decumbens*, a herbaceous annular historically employed by Taiwanese natives to harvest fish. In later publications, e.g., Ohta, et al., Tetrahedron Letters, No. 43, pp. 923–925 (1970); Chen, Proc. 5th Asian Congress Pharm. Sci. Fed., 1–7 Dec. 1974, pp. 79–86; the structure of justicidin A was assigned as set forth below:

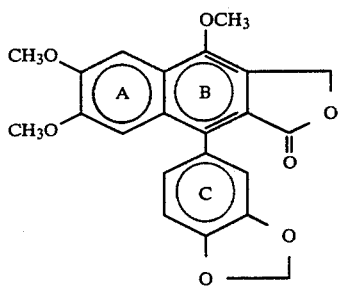

Justicidin B, which lacks the B-ring methoxy substituent of justicidin A, and a related compound are disclosed in Munakata, U.S. Pat. No. 3,704,247. This patent discloses that justicidin A and B exhibit extraordinary piscicidal activity, but does not disclose insecticidal activity, although synergistic behavior was observed when mixtures of justicidin A and B and pyrethrin or allethrin were tested against mosquito larvae of the species Culex pipiens pallens.

Ghosal, et al., Chem. and Ind., 854–855 (1979), described isolation and purification of prostalidins A, B and C from *Justicia prostata* C. B. Cl. Gamble, an antidepressant folk medicine. The structure of the prostalidins is set forth below:

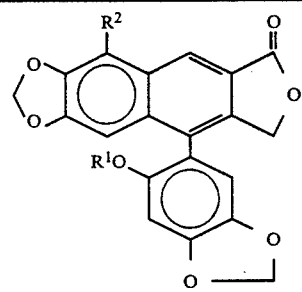

|  | R¹ | R² |
|---|---|---|
| Prostalidin A | H | OMe |

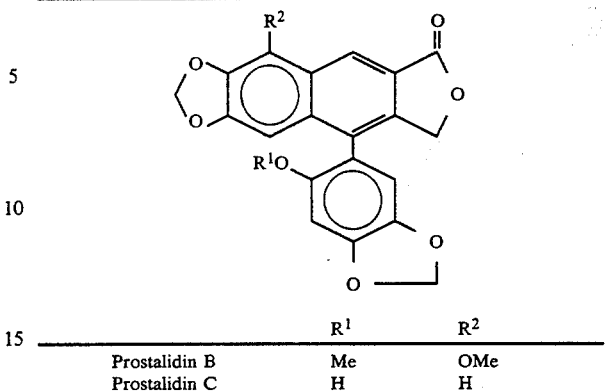

|  | R¹ | R² |
|---|---|---|
| Prostalidin B | Me | OMe |
| Prostalidin C | H | H |

Markannen, et al., Drugs Exptl. Clin. Res. VII(6): 711–718 (1981), disclose antiviral activity of certain podophyllotoxin lignans when tested against Herpes simplex Type-1 virus in mammalian cell cultures. However, none of the compounds tested by Markannen contain either an aromatic B-ring or a methoxylated lactone ring.

SUMMARY OF THE INVENTION

The invention is directed to a novel lignan known as Justicidin P and to a related class of compounds corresponding to the following formula:

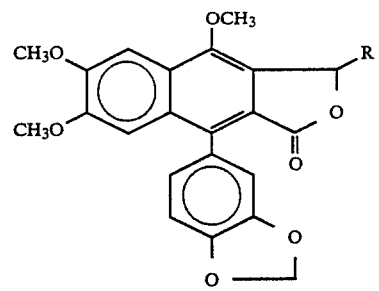

wherein

R is —F, —OOCCH$_3$, —OR$^1$, or —SR$^1$; where
R$^1$ is —H or an alkyl group of 1 to 12 carbon atoms, provided that when R is —OCH$_3$, the compound has the following physical properties:

(1) Melting point:
  natural product: 222° C. (cubes)
  synthetic: 208°–210° C.;

(2) Proton magnetic resonance spectra (CDCl$_3$):
  natural product: δ7.64 (S,1H), 7.05 (S,1H), 7.00–6.77 (m,3H), 6.57 (S,1H), 6.09(2S+, 2H), 4.23 (S,3H), 4.07 (S,3H), 3.80 (S,3H) and 3.68 (S,3H);
  synthetic product: δ7.48 (S,1H), 6.92 (S,1H), 6.86–6.66 (m,3H), 6.44 (S,1H), 5.97(2S+,2H), 4.16 (S,3H), 4.00 (S,3H), 3.72 (S,3H) and 3.59 (S,3H)

(3) Infrared absorption (CH$_2$Cl$_2$) maximum at 1740 cm$^{-1}$;

(4) Ultraviolet (ethanol) absorption maxima at 265, 295, 310 and 350 nm;

(5) Fluorescence maximum at 452 nm;

(6) Mass/charge ratio:
  natural product: 424.1163
  synthetic product: 424.1151;

and optical rotation for the natural product of $[\alpha]_D$ equal to $-107°$ (C=1.04, CHCl$_3$).

The invention is also directed to insecticidal and antiviral compositions containing the above described compounds, and to methods of using these compositions to kill insects, and to treat viral infections in mammals. In addition, the invention is directed to an intermediary compound useful in preparing other compounds of the invention.

DETAILED DESCRIPTION OF THE INVENTION

In accordance with the present invention, R$^1$ can be —H or an alkyl group of 1 to 12 carbon atoms; where R$^1$ is an alkyl group, R$^1$ can be an n-alkyl or a branched-chain alkyl group. Within the class of compounds of the present invention, it has been found that certain compounds are preferred because of an indication of greater insecticidal and/or antiviral effectiveness.

The preferred compounds of the invention for use in insecticidal compositions are those in which R is —OCH$_3$, —F, —OOCCH$_3$, —O-n-propyl, and —O-i-propyl. Particularly preferred are those in which R is —OCH$_3$ or —F.

The preferred compounds of the invention for use in treatment of viral infections are those in which R is —OCH$_3$, —F, —O-n-propyl, —O-i-propyl, and —SC$_7$H$_{15}$. The most preferred compound is that in which R is —OCH$_3$.

An additional feature of the invention is an intermediary compound, having a structural formula denoted 9, below, which is useful in a synthesis of the various compounds of the invention.

Justicidin P may be isolated from the leaves of *Justicia extensa* (family Acanthaceae) in the following manner: Leaves and branches of *Justicia extensa*, cultivated under greenhouse conditions, are harvested and freeze-dried. The lyophilized leaves are pulverized in a blender and the resulting powdery material suspended in a 50:50 (V/V) mixture of acetone and water. Typically about 2.5 ml of the aforementioned mixture are employed to extract each gram of dried leaf powder. After an extraction period of approximately 24 hours, supernatant is decanted, filtered and evaporated to dryness. Approximately 0.4 g of crude extract material are obtained for each gram of dried leaf powder.

The crude extract material obtained by the aforementioned extraction procedure is dissolved in a 40% (V/V) solution of ethyl acetate in n-hexane, at a ratio of approximately 0.1 g crude extract material per ml solvent. The resulting solution is applied to a 15.2×9.8 cm column containing silicic acid and eluted with approximately 8 l of the aforementioned ethyl acetate/n-hexane solvent. Serial fractions are collected and the resulting bands of colored material monitored visually as the column is eluted.

At a point approximately midway through the elution process, bands containing a blue fluorescent compound will be observed eluting from the column. The column fractions containing the blue flourescent compound are combined, evaporated to dryness under reduced pressure, and redissolved in a 40% solution (V/V) of ethyl actate in n-hexane, at a ratio of approximately 1 g dried material per ml solvent. Aliquots of 0.5 ml are applied to thin layer chromatography plates coated with a 250 micron layer of silica gel. The thin-layer plates are developed in 40% (V/V) ethyl acetate/n-hexane solvent and migration of the blue fluorescent band is observed visually, under ultraviolet light. At a point when a suitable separation has been achieved, the areas of the plates containing the blue fluorescent band are scraped and the resulting powdered absorbent eluted with acetone.

Aliquots of about 10 ml of the resulting solution are applied to 25×35 mm columns containing cross-linked dextran and eluted with additional acetone. Serial fractions are collected and fractions containing the blue fluorescent compound are combined.

Additional thin-layer chromatographic steps using solvents comprising between about 20 to about 50% (V/V) ethyl acetate in n-hexane can optionally be employed to purify the column fractions containing Justicidin P.

Finally, the purified product is eluted from the thin-layer bands exhibiting blue fluorescence and rcrystallized from ethyl acetate. Additional recrystallization steps can optionally be employed using ethyl acetate or mixtures of ethyl acetate and n-hexane varying between 20 and 50% (V/V) ethyl acetate in n-hexane. The resulting crystals of purified Justicidin P appear in two crystalline forms. One form appears as needle-like crystals, which form near the surface of the recrystallization solution. The second form appears as cube-like crystals, which form beneath the surface.

Justicidin P and related compounds of the present invention can be synthesized according to the following process. This particular process illustrates synthesis of Justicidin P:

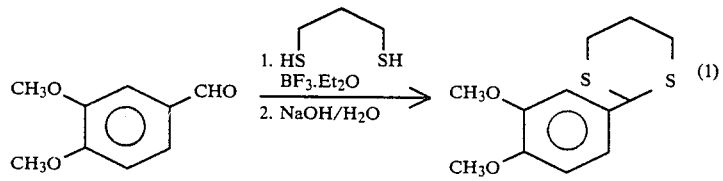

-continued
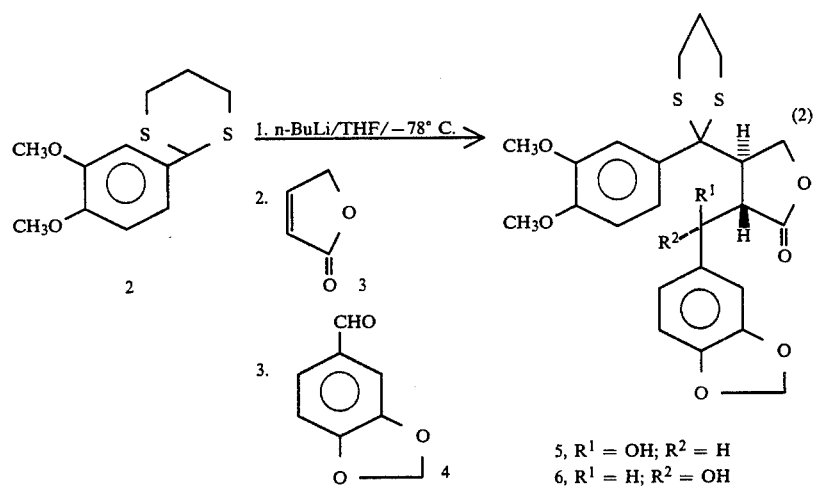
5, R$^1$ = OH; R$^2$ = H
6, R$^1$ = H; R$^2$ = OH
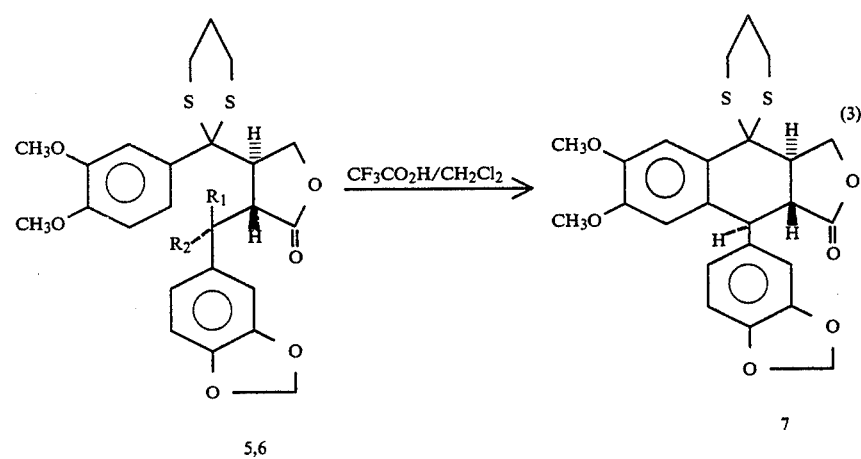
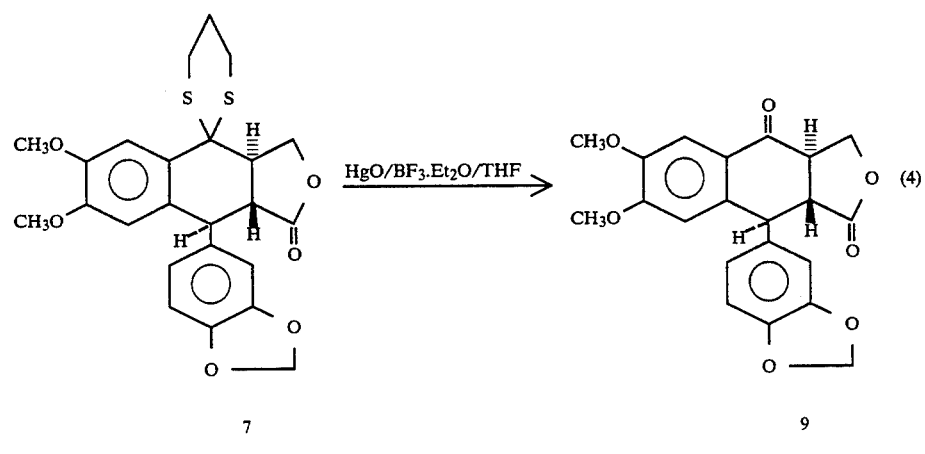

-continued

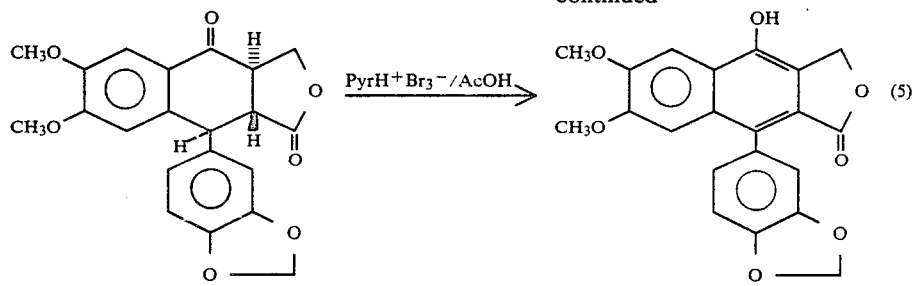

(5)

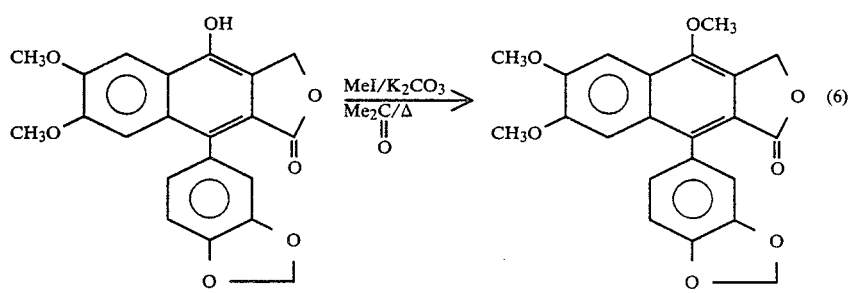

(6)

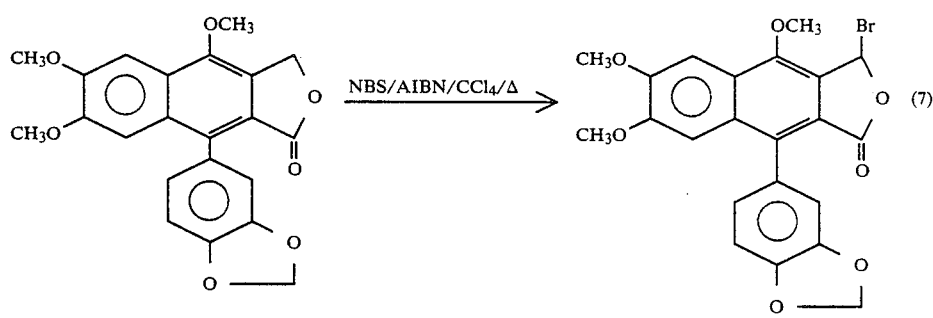

(7)

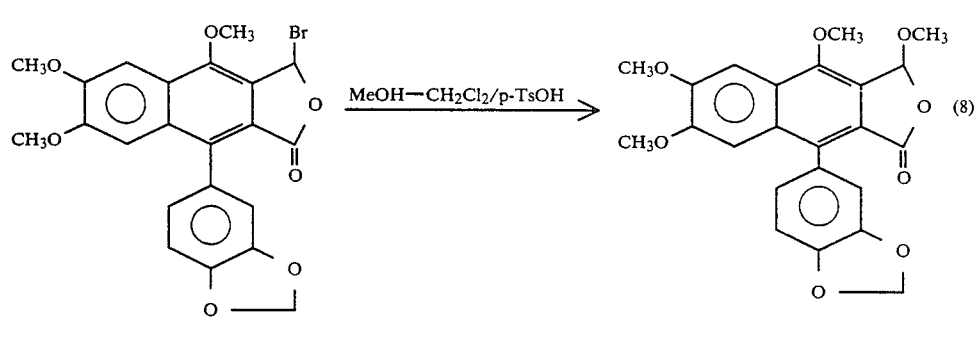

(8)

(1) Formation of 2-(3,4-Dimethoxyphenyl)-1,3-dithiane

The first step in the process for making Justicidin P can be conducted by adding boron trifluoride etherate ($BF_3 \cdot Et_2O$) to a solution containing 3,4-dimethoxybenzaldehyde and 1,3-propanedithiol in methylene chloride. After a suitable reaction time, the mixture is washed with a NaOH solution and a saturated solution of NaCl. The product is dried and then recovered by evaporation under reduced pressure.

(2) Ring Addition

The second step in the process is lithiation of the dithiane produced in step (1), above, and subsequent Michael addition of the lithiated dithiane to 2-butenolide, forming an unstable intermediate. Lithiation of 2-(3,4-dimethoxyphenyl)-1,3-dithiane by metal-hydrogen exchange can be effected with a variety of bases. Alkyl lithium reagents, for example, n-butyl lithium, are preferred for purposes of convenience. This step is conducted at about −78° C. to prevent decomposition of the resulting lactone enolate intermediate. The lactone enolate intermediate is then reacted immediately with a solution of 3,4-methylenedioxybenzaldehyde (piperonal) in tetrahydrofuran (THF) for approximately one hour, followed by quenching with 10% (V/V) aqueous acetic acid. After warming to about 23° C. and separation into aqueous and organic phases, the organic phase is washed with saturated NaCl and dried over MgSO$_4$. Tetrahydrofuran can then be removed by evaporation and the resulting product recovered by recrystallization from ethyl acetate.

The product of this reaction is obtained as a diastereomeric mixture. The threo and erythro diastereomers can be separated chromatographically. However, this step is unnecessary, since both diastereomers, upon treatment with trifluoroacetic acid in methylene chloride, provide the same cyclization product in the following reaction step.

This step in the process parallels work disclosed by Ziegler, et al., J. Org. Chem. 43: 985–991 (1978), in which 2-butenolide was added to a 1,3-dithiane derivative of piperonal and subsequently reacted with 3,4,5-trimethoxybenzaldehyde to produce (±)-isopodophyllotoxone dithiane.

(3) Cyclization Step

Cyclization of the B-ring of the product of step (2) is accomplished by reacting trifluoroacetic acid in methylene chloride with this product at about 23° C. This step also parallels work described by Ziegler, et al., J. Org. Chem. 43: 985–991 (1978), as well as that disclosed by Gonzalez, et al., Tetrahedron, 34: 1011–1013 (1978).

Although trifluoroacetic acid is a preferred reagent in this step of the process, other acidic or Lewis acid reagents can be employed. Following a reaction time of between about 3 hours and about 70 hours, crude product is precipitated from methylene chloride and can be further purified by preparative thin-layer chromatography and recrystallization from ethyl acetate.

(4) Hydrolysis of Dithiane

A preferred procedure for this step comprises hydrolysis of the dithiane product of Step 3 with mercuric oxide and boron trifluoride etherate in aqueous tetrahydrofuran. This reaction can be conducted at about 23° C.

The resulting product is recovered by precipitation from methylene chloride and subsequent purification can be accomplished by recrystallization from ethyl acetate. Other methods for hydrolysis of dithianes, known to those skilled in the art, can also be employed.

(5) Oxidation of the B-Ring

In this step, the product of step (4) is contacted with pyridinium bromide perbromide (PyrH$^+$Br$_3^-$) in acetic acid, forming a reaction mixture. After 15 to about 40 hours at about 23° C., the reaction mixture is diluted with ethyl acetate. The resulting crude product can be further purified by preparative thin-layer chromatography using ethyl ether as solvent. The product of this step, 9-(1,3-benzodioxol-5-yl)-6,7-dimethoxy-4-hydroxynaptho-[2,3-c]furan-1(3H)-one, is also known as diphyllin.

(6) Methylation of the B-ring Phenol

This step converts the product of step (5), diphyllin, to justicidin A, via methylation of the B-ring phenol. A preferred method for conducting this reaction involves a reaction of diphyllin with methyl iodide and potassium carbonate in acetone at about 60° C. Other methods known for such transformations, involving other bases and other methylating agents, can optionally be employed.

The resulting product can be further purified by preparative thin layer chromatography and recrystallization from chloroform-ether.

(7) Bromination of the Lactone Ring at the 3-position

This step provides starting material for synthesis of a number of compounds related to Justicidin P which vary with respect to substituents at the 3-position of the lactone ring of justicidin A. The product of step (6), justicidin A, is subjected to radical bromination with N-bromosuccinimide (NBS). The radical bromination reaction is conducted for a suitable period at about 80° C. A preferred radical initiator for this step is azobisisobutyronitrile (AIBN), since it provides bromide in high yield. Other radical initiators, such as benzoyl peroxide, can optionally be employed.

After solvent removal, crude product is immediately subjected to the next step, in which various functional subgroups or atoms are exchanged for the bromine atom at the 3-position.

(8) Functionalization of the Lactone Ring

In this step, the bromine atom at the 3-position of the lactone ring is exchanged for varying functional subgroups or atoms, which can include methoxy, acetyloxy, fluoride, n-alkoxy, branched chain alkoxy, or various thioalkyl derivatives.

In the illustrated reaction, in which a methoxy group is exchanged for the bromine atom at the 3-position of the lactone ring to produce Justicidin P, the crude product of the foregoing bromination step is dissolved in a solvent mixture of methanol and methylene chloride and reacted with trimethyl orthoformate and para-toluenesulfonic acid (p-TsOH) at about 23° C. Following solvent removal, the resulting crude enantiomeric product mixture can be further purified by preparative thin-layer chromatography.

The compounds of the invention and processes for their synthesis are further described in the following examples. In the examples, percentages of aqueous solutions are weight/volume; percentages of solvent mixtures, such as those used in chromatographic steps, are volume/volume. All other percentages indicated are weight/weight.

Proton and carbon-13 NMR (PMR and CMR) chemical shifts are given in delta ($\delta$) units, parts per million from internal reference tetramethylsilane, in which a downfield shift from the reference is taken as positive. All temperatures are reported in degrees Celsius.

The compounds of the invention, as synthesized by the foregoing process, occur as racemic mixtures of d and l optical isomers, which can be resolved by known methods (Eliel, Stereochemistry of Carbon Compounds, McGraw-Hill, 1962, p. 21).

EXAMPLE 1: Justicidin P

A. 2-(3,4-Dimethoxyphenyl)-1,3-dithiane (2)

Boron trifluoride etherate (13 ml) was added slowly to a solution of 3,4-dimethoxybenzaldehyde (1; 50 g, 0.30 mol) and 1,3-propanedithiol (33 ml, 0.33 mol) in methylene chloride (200 ml). The resulting mixture was stirred at about 23° for 22 hr; washed with 3N sodium hydroxide and saturated sodium chloride, and dried over magnesium sulfate. Evaporation of solvent under reduced pressure and removal of excess 1,3-propanedithiol on a steam bath provided a crystalline product which was washed with ethyl ether to give 64 g (83%) of 2-(3,4-dimethoxyphenyl)-1,3-dithiane, a white crystalline material. PMR (CDCl$_3$): δ7.20–6.76 (m, 3H), 5.17 (s, 1H), 3.91 (s, 3H), 3.87 (s, 3H), 3.20–2.85 (m, 4H), and 2.25–1.67 (m, 2H).

B. [3α(R*),4β]- and [3α(S*), 4β]-(±)-[1,3-Benzodioxol-5-yl)-hydroxymethyl]-4,5-dihydro-4-[2-(3,4-dimethoxyphenyl)-1,3-dithian-2-yl)-2(3H)-furanone (5 and 6, respectively; erythro and threo, respectively)

To a solution of 2 (1.28g, 5 mmol) in tetrahydrofuran (THF, 10 ml) at −78° was slowly added n-butyl lithium (1.6M, 3.2 ml, 5.1 mmol). An orange solution was initially formed. Following the addition, a white precipitate formed. The resulting mixture was stirred for 30 min, followed by addition of a solution of 2-butenolide (3, 420 mg, 5 mmol; prepared according to the procedure in Organic Syntheses, Collective Volume V, p. 256) in THF (2 ml) over 20 min. The reaction mixture was stirred for 30 min and then treated with 3,4-methylenedioxybenzaldehyde (4, 750 mg, 5 mmol) in 3 ml of THF. After an additional hour, the reaction was quenched with 10% (V/V) aqueous acetic acid and allowed to warm to room temperature. Ethyl acetate was added, and after separation of aqueous and organic phases, the resulting organic phase was washed with saturated sodium chloride and dried over magnesium sulfate. Removal of solvent followed by recrystallization from ethyl acetate gave a first crop, 214 mg, consisting predominately of 5; a second crop, 419 mg, a mixture of 5 and 6; and a third crop, 371 mg, also a mixture.

The foregoing procedure was repeated on a 20 mmol scale. The crude product was recrystallized from ethyl acetate to afford 2.64 g of [3α(R*), 4β]-(±)-3-[(1,3-benzodioxol-5-yl)-hydroxymethyl]-4,5-dihydro-4-[2-(3,4-dimethoxyphenyl)-1,3-dithian-2-yl]-2(3H)-furanone, 5. The mother liquor was purified by high performance liquid chromatography on silica using ethyl acetate-pentane (1:1) as eluent to provide an additional 0.33 g of 5 and 1.49 g of [3α(S*),4β]-(±)-3-[(1,3-benzodioxol-5-yl)-hydroxymethyl]-(4,5)-dihydro-4-[2-(3,4-dimethoxyphenyl)-1,3-dithian-2-yl]-2(3H)-furanone, 6.

Physical data for erythro product, 5: mp, 215°–216° (recrystallized from ethyl acetate-methanol); IR (CH$_2$Cl$_2$): 3500, 1775, and 1601 cm$^{-1}$; PMR (CDCl$_3$): δ7.30 (bd, J=7 Hz, 1H), 7.02 (bs, 1H), 6.61 (d, J=7 Hz, 1H), 6.59 (s, 2H), 6.24 (bs, 1H), 5.98 (bs, 1H), 5.92 (bs, 1H), 5.00 (m, 1H), 4.89 (bd, J=9 Hz, 1H), 4.32 (t, J=9 Hz, 1H), 3.87 (s, 3H), 3.71 (s, 3H), and 2.95–1.82 (m, 8H); Anal. Calcd. for C$_{24}$H$_{26}$O$_7$S$_2$, C, 58.76; H, 5.34; found, C, 58.33; H, 5.17.

Physical data for threo product, 6: mp, 136°–138° (recrystallized from ethyl acetate-petroleum ether); IR (CH$_2$Cl$_2$): 3500, 1775, and 1601 cm$^{-1}$; PMR (CDCl$_3$): δ7.42 (bd, J=9 Hz, 1H), 7.18 (d, 1H), 6.80 (d, J=9 Hz, 1H), 6.64–6.48 (m, 3H), 5.95 (bs, 1H), 5.89 (bs, 1H), 4.74 (bd, J=8 Hz, 1H), 4.61 (d, J=7 Hz, 1H), 3.98 (t, J=7 Hz, 1H), 3.88 (s, 3H), 3.74 (s, 3H), and 3.09–1.73 (m, 8H); Anal. Found, C, 58.33; H, 5.18.

C. (±)-9′β-(1,3-Benzodioxol-5-yl)-3′,3′aα,9′,9′aβ-tetrahydro-6′,7′-dimethoxyspiro[1,3-dithiane-2,4′(1′H)-naphtho[2,3-c]furan]-1′-one (7) (from erythro, 5)

A solution of 5 (erythro) (400 mg, 0.81 mmol) in methylene chloride (10 ml) containing 2 ml of trifluoroacetic acid was stirred at about 23° C., forming a reaction mixture. After about 68 hr, the reaction mixture was poured into saturated sodium bicarbonate. After separating organic and aqueous layers, the aqueous layer was extracted once with methylene chloride. The methylene chloride extract and the organic layer of the preceding step were combined, washed with saturated sodium chloride, and dried over magnesium sulfate. The resulting crude product was purified by preparative thin-layer chromatography to provide 289 mg of (+)-9′β-(1,3-benzodioxol-5-yl)-3,3′aα,9′,-9′aβ-tetrahydro-6′,7′-dimethoxyspiro[1,3-dithiane-2,4′(1′H)-naphtho[2,3-c]-furan-1′-one, 7. Recrystallization from ethyl acetate provided 118 mg of white solid, 7a. mp: 202°–206°; IR (CH$_2$Cl$_2$): 1790 and 1610 cm$^{-1}$; PMR (CDCl$_3$): δ7.64 (s,1H), 6.75 (s, 2H), 6.61 (s, 1H), 6.20 (s, 1H), 5.92 (s, 2H), 4.77–2.00 (m, 11H), 3.93 (s, 3H), and 3.60 (s, 3H); CMR (see CMR of 7a prepared in Part D of Example 1); Anal. Calcd for C$_{24}$H$_{24}$O$_6$S$_2$, C, 60.99; H, 5.12; found, C, 60.26; H, 5.01.

A separate sample of product 7b, mp 146°–148° (recrystallized from ethyl acetate-petroleum ether) was prepared by substantially the foregoing procedure except that the reaction mixture was stirred for 22 hr. This sample was submitted for analysis. CMR (CDCl$_3$-TMS): δ175.018, 149.282, 147.852, 146.552, 137.064, 132.644, 131.410, 123.026, 112.237, 112.107, 109.313, 108.143, 100.994, 68.824, 56.801, 56.021, 55.761, 52.447, 46.078, 44.518, 30.675, 29,310, 23.721; IR, PMR (see spectra of 7b prepared in Part D, below); Anal. Found, C, 60.42; H, 5.45. The two samples obtained, 7a and 7b above, have different melting points. This can be attributed to the two crystalline forms which were isolated. The spectra of the two crystalline forms in solution are substantially identical.

D. (±)-9′β-(1,3-Benzodioxol-5-yl)-3′,3′aα,9′,9′aβ-tetrahydro-6′,7′-dimethoxyspiro[1,3-dithiane-2.4′ (1′H)-naphtho[2,3-c)]furan]-1′-one (7) (from threo, 6)

A solution of 6 (490 mg, 1 mmol) in methylene chloride (20 ml) containing 2 ml of trifluoroacetic acid was stirred at room temperature for 3 hr. Using a procedure similar to that described in Part C of this example, 480 mg of crystalline product [9′β-(1,3-benzodioxol-5-yl)-3a′α,9′-dihydro-6′,7′-dimethoxyspiro [1,3-dithiane-2,4′(1′H)-naphtho[2,3-c]furan]-1′-one(3′a,-9′α,9′aβ) 7b were obtained after recrystallization from ethyl acetate-hexanes, mp 146°–151°. IR (CH$_2$Cl$_2$): 1780, 1610 cm$^{-1}$; PMR (CDCl$_3$): δ7.63 (s, 1H), 6.73 (s, 2H), 6.59 (s, 1H), 6.19 (s, 1H), 5.90 (s,2H), 4.75–2.00 (m, 11H), 3.91 (s, 3H), and 3.59 (s, 3H); CMR (see CMR of 7b prepared in Example 3); Anal. Calcd. for C$_{24}$H$_{24}$O$_6$S$_2$, C, 60.99; H, 5.12; found C, 60.61; H, 5.10.

In another run 5 g of 6 were dissolved in methylene chloride (150 ml) and treated with 7 ml of trifluoroacetic acid at about 23° for 22 hr. After using a procedure similar to that described in Part C of this example, activated carbon was added to decolorize the resulting methylene chloride layer. Recrystallization of the resulting crude product from ethyl acetate-petroleum ether yielded 3.8 g of 7a, mp 196°-200°. CMR (CDCl$_3$): δ175.018, 149.282, 147.722, 146.552, 137.064, 132.644, 131.345, 123.026, 112.107 (2 peaks), 109.248, 108.143, 100.994, 68.824, 56.801, 55.826 (2 peaks), 52.447, 46.078, 44.453, 30.675, 29.310, 23.656; PMR, IR (see spectra of 7a prepared in Part C).

The two samples obtained exhibited different melting points, which can be attributed to the two different crystalline forms which were obtained. These are the same high-melting and low-melting forms obtained in Part C. Either 7a or 7b may be synthesized under virtually identical conditions, from either the erythro (5), or the threo (6), precursor.

E. [3aα, 9α, 9aβ]-(±)-9-(1,3-Benzodioxol-5-yl)-6,7-dimethoxy-3,3a,9,9a-tetrahydronaphtho[2,3-c]-furan-1,4-dione (9)

To a solution of 2 ml of 15% aqueous tetrahydrofuran was added 87 mg (0.4 mmol) of red mercuric oxide followed by 56 mg (0.4 mmol) of boron trifluoride etherate. Then a solution of 7 (106 mg, 0.2 mmol) in 10 ml of THF was added. Either 7a or 7b, above, can be employed. The resulting mixture was stirred at about 23° for 3 hr. Methylene chloride was added followed by filtration of precipitated salts. The filtrate was washed with saturated sodium carbonate, saturated sodium chloride and then dried over magnesium sulfate. Evaporation of solvent provided 88 mg of product which, upon addition of ethyl acetate, crystallized to provide approximately 20 mg of 3aα,9α,9aβ]-(±)-9-(1,3-benzodioxol-5-yl)-6,7-dimethoxy-3,3a,9,9a-tetrahydronaphtho[2,3-c]furan-1,4-dione, 9, as a white crystalline compound, and 63 mg of additional product from the mother liquor. The white crystalline product was characterized by IR (CHCl$_3$): 1780, 1690, and 1595 cm$^{-1}$; and PMR (CDCl$_3$): δ7.43-6.25 (m, 5H), 5.99 (s, 1H), 5.95 (s, 1H), 3.79 (s,3H), 3.55 (s, 3H), and 4.82-2.00 (m, 5H).

In another run the mixture was stirred at room temperature for 22 hr. From 140 mg of 7 was obtained 93 mg of 9, mp 253°-256°. MS: m/z 382.1064 (M+).

F. 9-(1,3-Benzodioxol-5-yl)-6,7-dimethoxy-4-hydroxynaphtho[2,3-c]furan-1(3H)-one (10; Diphyllin)

A mixture of 9 (10 mg, 0.026 mmol) in acetic acid (1 ml) containing pyridinium bromide perbromide (10 mg, 0.0312 mmol) was stirred at about 23° for 20 hr and then at 45° for 3 hr. The mixture was then diluted with ethyl acetate, washed with saturated sodium bicarbonate and saturated sodium chloride, and dried over magnesium sulfate. Thin-layer chromatography of the resulting crude product, using ethyl ether as a developing solvent, showed two spots. A more polar one (2 mg after purification by preparative thin-layer chromatography), which exhibited blue fluorescence under ultraviolet light, was the desired product 9-(1,3-benzodioxol-5-yl)-6,7-dimethoxy-4-hydroxynaphtho[2,3-c]furan-1(3H)-one 10. The less polar one (8 mg) was partially converted to the desired product during its isolation from the thin layer plate. This less polar material was dissolved in 1 ml of toluene and treated with 1 drop of 1,5-diazabicyclo[5.4.0]-undec-5-ene at 0° for 15 min. It was diluted with methylene chloride, washed with 10% aqueous hydrogen chloride and saturated sodium chloride, and dried over magnesium sulfate. In this manner, 5.4 mg of additional product was isolated. Another sample of the product, prepared by substantially the foregoing procedure, was submitted for analysis. IR (Nujol): 1710 and 1620 cm$^{-1}$; PMR [(CD$_3$)$_2$SO]: δ7.50 (s, 1H), 6.93-6.61 (m, 4H), 6.02 (s, 2H), 5.27 (s, 2H), 3.88 (s, 3H), 3.60 (s, 3H); MS: m/z 380.0873 (M+); calcd. for C$_{21}$H$_{16}$O$_7$, 380.0893. Yet another sample was recrystallized from ethanol to give a sample with mp 280°-282° (darkening at 259°).

G. 9-(1,3-Benzodioxol-5-yl)-4,6,7-trimethoxynaphtho[2,3-c]furan-1(3H)-one (11; Justicidin A)

The product of step F, diphyllin, (10; 75 mg; 0.197 mmol), and 1 ml methyl iodide were dissolved in 5 ml acetone containing 82 mg potassium carbonate (0.6 mmol), and the resulting solution heated at about 60° for one hour. After removing acetone, a residue remained which was treated with methylene chloride and 10% aqueous hydrogen chloride. After separation of aqueous and organic layers, the organic layer was washed with saturated sodium chloride and dried over magnesium sulfate. Evaporation of solvent and purification on a preparative thin-layer chromatography plate provided ca. 67 mg of 9-(1,3-benzodioxol-5-yl)-4,6,7-trimethoxynaphtho[2,3-c]furan-1-(3H)-one, 11, mp 248°-250°. IR(CHCl$_3$): 1770, 1620 cm$^{-1}$; PMR (CDCl$_3$): δ7.39 (s, 1H), 6.91 (s, 1H), 6.83-6.64 (m, 3H), 5.94 (2s, 2H), 5.42 (s, 2H), 4.05 (s, 3H), 3.98 (s, 3H), and 3.73 (s, 3H); MS: m/z 394.1006 (M+), calcd. for C$_{22}$H$_{18}$O$_7$, 394.1049. A separate sample of product 11, prepared by substantially the foregoing procedure, was recrystallized from chloroform-ether, mp 256°-258°. This crystalline product was again recrystallized from chloroform-ether, mp 258°-260°.

H. (±)-9-(1,3-Benzodioxol-5-yl)-3,4,6,7-tetramethoxynaphtho[2,3-c]furan-1(3H)-one (13; Racemic Justicidin P)

A mixture of 11 (25 mg, 0.063 mmol) in carbon tetrachloride (2 ml) containing N-bromosuccinimide (22 mg, 0.127 mmol) and benzoyl peroxide (5 mg) was heated at ca. 85° for 30 min. After removing solvent, the resulting residue (crude 12) was dissolved in methanol-methylene chloride (0.5/2 ml) and treated with ten drops of trimethyl orthoformate and 10 mg of para-toluenesulfonic acid at about 23° for 3 hr. Removal of solvent and purification on a thin-layer plate provided 6 mg of product, (±)-9-(1,3-benzodioxol-5-yl)3,4,6,7-tetramethoxynaphtho[2,3-c]furan-1-(3H)-one, 13, racemic Justicidin P, mp 208°-210° (202° decomp. begins). PMR (CDCl$_3$): δ7.48 (s, 1H), 6.92 (s, 1H), 6.86-6.66 (m, 3H), 6.44 (s, 1H), 5.97 (2s, 2H), 4.16 (s, 3H), 4.00 (s, 3H), 3.72 (s, 3H), and 3.59 (s, 3H); UV (EtOH); 264, 295, 309, and 350 nm; fluorescence, 453 nm; MS: m/z 424.1151 (M+); calcd. for C$_{23}$H$_{20}$O$_8$, 424.1155. A separate sample of product 13, prepared by substantially the foregoing procedure, was submitted for IR (CH$_2$Cl$_2$): 1740 cm$^{-1}$.

By substituting azobisisobutyronitrile for benzoyl peroxide and following substantially the foregoing procedure, yield of 13 was increased to 71%.

Table 1, below, lists reagents which can be employed in reactions similar to the functionalization reaction of step H to synthesize certain analogues of Justicidin P varying at the 3-substituted position, R in the following formula:

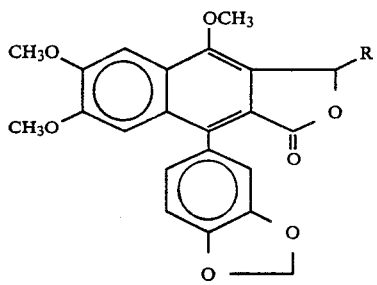

TABLE 1

Synthetic Analogues of Justicidin P

| Example | Compound | R | Reagent |
|---|---|---|---|
| 1 | Justicidin P | —OCH$_3$ | (CH$_3$O)$_3$CH/MeOH/p-TsOH |
| 2 | 14 | —F | AgF |
| 3 | 15 | —OAc | AgOAc |
| 4 | 16 | —OH | H$_2$O/p-TsOH |
| 5 | 17 | —O—n-Pr | n-PrOH/p-TsOH |
| 6 | 18 | —S—n-C$_7$H$_{15}$ | n-C$_7$H$_{15}$SH/p-TsOH |
| 7 | 19 | —O—i-Pr | i-PrOH/p-TsOH |
| 8 | 20 | —O—n-C$_{12}$H$_{25}$ | n-C$_{12}$H$_{25}$OH/p-TsOH |

EXAMPLE 2

(±)-9-(1,3-Benzodioxol-5-yl)-3-fluoro-4,6,7-trimethoxynaphtho[2,3-c]furan-1(3H)-one (14)

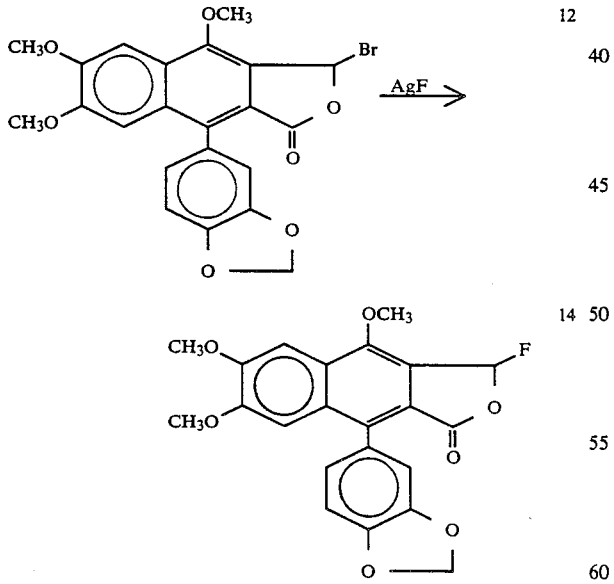

A mixture of 11 (100 mg, 0.25 mmol) in carbon tetrachloride (20 ml) containing N-bromosuccinimide (54 mg, 0.3 mmol) and azobisisobutyronitrile (10 mg) was heated at ca. 80° for 1.5 hr. Solvent was removed and the resulting crude product 12 divided into two equal portions. One half was dissolved in acetonitrile (3 ml) and treated with silver fluoride (80 mg, 0.625 mmol) at about 23°, in the dark, for 1.5 hr. Additional silver fluoride (ca. 40 mg) was added and the resulting mixture was stirred continuously for another hour. After adding sodium chloride, the mixture was filtered through diatomaceous earth and washed with methylene chloride during filtration. The filtrate was then washed with saturated sodium bisulfite and saturated sodium chloride, and dried over magnesium sulfate. The resulting crude product 14 was purified by preparative thin layer chromatography using ethyl acetate-petroleum ether (1:1) as eluent to provide 24 mg of (±)-9-(1,3-benzodioxol-5-yl)-3-fluoro-4,6,7-trimethoxynaphtho[2,3-c]furan-1(3H)-one, 14. PMR (CDCl$_3$): δ7.54–6.66 (m, 6H), 6.00 (s, 1H), 5.95 (s, 1H), 4.20 (s, 3H), 3.98 (s, 3H), and 3.71 (s, 3H).

EXAMPLE 3

(±)-9-(1,3-Benzodioxol-5-yl)-3-acetyl-4,6,7-trimethoxynaphtho[2,3-c]furan-1(3H)-one (15)

The other half of crude 12 prepared in Example 2 was dissolved in acetonitrile (3 ml) and treated with silver acetate (110 mg, 0.625 mmol) at about 23°, in the dark, for 1.5 hr. Additional silver acetate (ca. 50 mg) was added and the resulting reaction mixture was stirred continuously for another hour. After adding sodium chloride, the mixture was filtered through diatomaceous earth and washed with methylene chloride during filtration. The resulting filtrate was then washed with saturated sodium chloride and dried over magnesium sulfate to provide crude product 15, which was purified on a preparative thin-layer plate using ethyl acetate-petroleum ether (1:1) as eluent to give 16.9 mg of (±)-9-(1,3-benzodioxol-5-yl)-3-acetyl-4,6,7-trimethoxynaphtho[2,3-c]furan-1 (3H)-one, 15. PMR (CDCl$_3$): δ7.71 (s, 1H), 7.55 (s, 1H), 7.05 (s, 1H), 7.00–6.77 (m, 3H), 6.07 (s, 1H), 6.02 (s, 1H), 4.10 (s, 3H), 4.05 (s, 3H), 3.80 (s, 3H), and 2.20 (s, 3H).

EXAMPLE 4

(±)-9-(1,3-Benzodioxol-5-yl)-3-hydroxy-4,6,7-trimethoxynaphtho[2,3-c]furan-1(3H)-one (16)

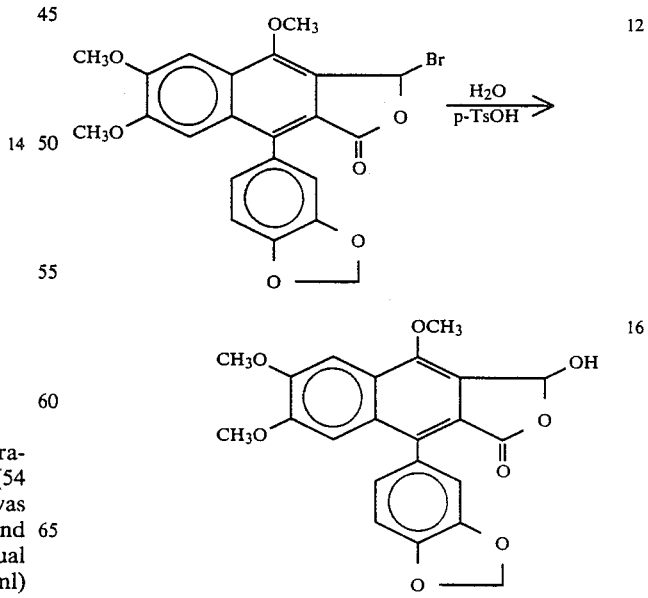

Crude bromide 12 (45 mg), prepared by N-bromosuccinimide reaction of 11, was treated with para-toluenesulfonic acid (10 mg) in tetrahydrofuran/water (1 ml/1 ml) at about 23° for 15 hr. The resulting mixture was diluted with methylene chloride, washed with saturated sodium chloride, and dried over magnesium sulfate. Evaporation of solvent afforded 32 mg of (±)-9-(1,3-benzodioxol-5-yl)-3-hydroxy-4,6,7-trimethoxynaphtho[2,3-c]furan-1(3H)-one, 16. IR (neat): 3440, 3300, 1760, 1705, and 1605 cm$^{-1}$: PMR (CDCl$_3$): δ7.53 (s, 1H), 7.00–6.60 (m, 5H), 6.03 (bd, 2H), 4.67 (m, 1H), 4.26 (s, 3H), 4.03 (s, 3H), and 3.73 (s, 3H); MS: m/z 410.1036; calcd. for C$_{22}$H$_{18}$O$_8$, 410.0999.

EXAMPLE 5

(±)-9-(1,3-Benzodioxol-5-yl)-3-propoxy-4,6,7-trimethoxynaphtho[2,3-c]furan-1(3H)-one (17)

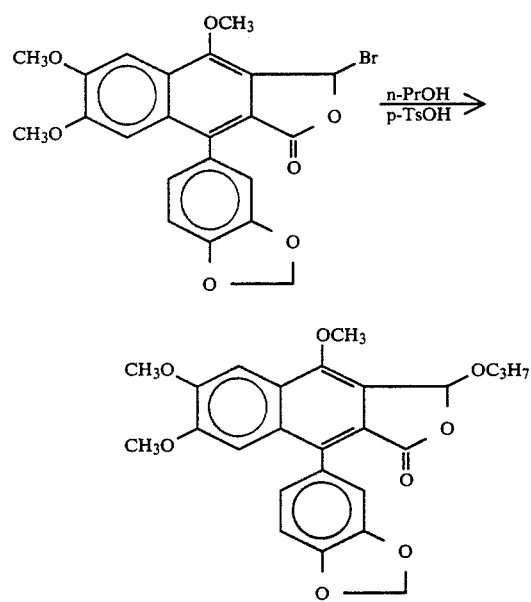

A mixture of 11 (50 mg, 0.125 mmol) in carbon tetrachloride (10 ml) containing N-bromosuccinimide (27 mg, 0.15 mmol) and azobisisobutyronitrile (10 mg) was heated at ca. 80° for one hour to provide crude product 12. Solvent was removed and crude product 12 was dissolved in methylene chloride and n-propanol (2 ml/1 ml) and reacted with para-toluenesulfonic acid (10 mg) at about 23° overnight. After removal of solvent, a residue remained, which was diluted with methylene chloride, washed with saturated sodium bicarbonate and saturated sodium chloride, and dried over magnesium sulfate, to give a crude product. This crude product was purified on preparative thin-layer plates using ethyl acetate-petroleum ether (1:1) as eluent, giving 33 mg of (±)-9-(1,3-benzodioxol-5-yl)-3-propoxy-4,6,7-trimethoxynaphtho[2,3-c]-furan-1(3H)-one, 17. PMR (CDCl$_3$): δ7.59 (s, 1H), 7.01 (s, 1H), 7.00–6.73 (m, 3H), 6.59 (s, 1H), 6.04 (q, 2H), 4.22 (s, 3H), 4.06 (s, 3H), 3.78 (1s & m, 3H & 2H), 1.70 (m, 2H), and 1.00 (t, 3H). A separate sample of 17, prepared by substantially the foregoing procedure, had IR(CH$_2$Cl$_2$): 1775 cm$^{-1}$; MS: m/z 452.1473 (M+); calcd. for C$_{25}$H$_{24}$O$_8$: 452.1470.

EXAMPLES 6, 7, 8

Compounds 18, 19, and 20 were each prepared by a procedure substantially similar to that described in Example 5, substituting the reagent shown in Table 2 for the n-propanol used in the example.

TABLE 2

| Compound | Reagent | R | Mass Spectrum (m/z) |
|---|---|---|---|
| 18 | n-C$_7$H$_{15}$SH | S—n-C$_7$H$_{15}$ | 524.1831 |
| 19 | i-PrOH | O—i-Pr | 452.1472 |
| 20 | n-C$_{12}$H$_{25}$OH | O—n-C$_{12}$H$_{25}$ | 578.2822 |

UTILITY

Insecticidal Activity

The compounds of the invention may be applied to insects by direct contact, by solution in water in which larvae subsist, or by formulation into solid dusts for application to crops or animal feeds, to control insect feeding activity.

The insecticidal activity of the crude acetone/water extracts of *Justicia extensa*, prepared according to the isolation procedure described previously, was tested against laboratory cultures of the mosquito species *Aedes egypti* (Linnaeus) and southern army worm (SAW) *Spodoptera eridania* (Cramer). Extracts of leaves, branches and roots were employed in each test.

In tests against larvae of *A. egypti*, 10 mg of the crude plant extract was thoroughly dispersed in 20 ml of water in a test tube to which 10 first instar larvae were added. Mortality and other effects of the treatment were observed daily. The results of these tests are set forth in Table 3 below:

Table 3

Mortality (%) of *Aedes egypti* larvae exposed to crude extracts of *Justicia extensa* at a concentration of 0.5 mg/ml (ca. 500 ppm)

| Plant part | Days following treatment | | |
|---|---|---|---|
| | 1 | 2 | 3 |
| Leaves | 100 | 100 | 100 |
| Stems | 60+ | 0* | 100 |
| Roots | 60+ | 0* | 100 |
| Controls | 0 | 0 | 0 |

*The larvae were observed to be smaller, indicating inhibited growth.
+Larvae may have been too small or immobile to give a positive response in the mortality determination, which was based upon observations of larval mobility.

Tests of crude extracts of *J. extensa* against SAW were performed by mixing 50 mg of crude plant extract, prepared as previously indicated, into 5 g of an artificial pinto bean diet composition, as described by Shorey, (J. Econ. Entomol. 56: 536–537, (1963)). Ten SAW larvae were placed into a container with the test diet mixtures, and observed for mortality, growth relative to the control larvae, and food consumption. The results of these tests are presented in Table 4 below:

TABLE 4

Mortality, relative size, and feeding response of *Spodoptera eridania* exposed to diet containing crude extracts of *Justicia extensa* at 0.5% (W/W)

| Plant Part | Day 2 | | | | Day 3 | | | | Day 4 | | | | Mortality % | Feeding Inhibition % |
|---|---|---|---|---|---|---|---|---|---|---|---|---|---|---|
| | L | D | S | F | L | D | S | F | L | D | S | F | | |
| Leaves | 10 | 0 | ± | ± | 10 | 0 | ± | ± | 9 | 0 | + | + | 10 | 90 |
| Stems | 10 | 0 | ± | ± | 10 | 0 | ± | ± | 10 | 0 | + | + | 0 | 90 |
| Roots | 10 | 0 | ± | ± | 10 | 0 | ± | ± | 10 | 0 | + | + | 0 | 80 |
| Control | 10 | 0 | ± | ± | 10 | 0 | 2+ | 2+ | 10 | 0 | 5+ | 5+ | 0 | 0 |

Notes:
L: Live larvae
D: Dead larvae
S: Relative larvae size compared to control larvae
F: Food consumed relative to control larvae
±: No detectable difference
+: Qualitive estimate on scale of 1–5+

The results of the insecticidal tests of crude extracts of *J. extensa* demonstrate insecticidal and feeding inhibition activity when applied to *A. egypti* and SAW. Extracts of leaves exhibit higher potency than extracts of stems or roots.

Further tests of insecticidal and feeding inhibition activity at lower concentrations, using purified fractions prepared substantially as previously described, demonstrated that Justicidin P is an insecticidal component of the *J. extensa* extracts.

When tested against larvae of *A. egypti*, the purified crystalline isolate of Justicidin P demonstrated an $EC_{50}$ (effective kill concentration for 50% of the experimental larvae) of 0.05 ppm. At levels of 1, 10, and 100 µg/gm of purified Justicidin P in pinto bean diet, 20%, 10%, and 60% kill and 62%, 77%, and 85% feeding inhibition, respectively, were observed in tests with SAW. When a spray containing 2.0 mg/ml purified Justicidin P in water was applied to SAW, 85% feeding inhibition but 0% kill was observed.

The insecticidal activities of various synthetic analogues of Justicidin P were tested against larvae of *A. egypti* in a manner similar to that described for the crude and partially purified extracts, above. The results of these experiments for the compounds corresponding to the following formula are set forth in Table 5, below:

TABLE 5

Insecticidal Activity ($EC_{50}$) of Justicidin P Analogues Against Larvae of *A. egypti* in $H_2O$

| Compound | R | $R^1$ | $EC_{50}$ (ppm) |
|---|---|---|---|
| Justicidin P | —OCH$_3$ | —CH$_3$ | 0.05 natural |
| Justicidin P | —OCH$_3$ | —CH$_3$ | 0.01 synthetic |
| Justicidin A | —H | —CH$_3$ | 10.0 |
| Diphyllin | —H | —H | not active |
| 14 | —F | —CH$_3$ | 0.7 |
| 15 | —OAc | —CH$_3$ | 1.0 |
| 16 | —OH | —CH$_3$ | 10.0 |
| 17 | —O—n-Pr | —CH$_3$ | 0.8 |
| 19 | —O—i-Pr | —CH$_3$ | 0.7 |

Antiviral Activity

The compounds of the invention may be employed in the treatment of viral infections in mammals, by formulating compositions of pharmaceutically suitable carriers known in the art with various compounds of the invention in amounts effective to inactivate the infective virus.

The antiviral activity of Justicidin P and its analogues was tested against Herpes Type 1-strain VR3, Herpes Type 2-Alabama strain, Human rhinovirus HRV-2 and vesicular stomatitis virus (VSV). These tests and the culturing of mammalian host cells and infective virus were conducted according to procedures similar to those routinely followed in established laboratories.

The tests involving Herpes Type 1-strain VR3 and Herpes Type 2-Alabama strain were carried out using HeLa cells, or occasionally, IMR-90 cells. HeLa cells were grown in roller bottles in 90% Eagles minimal essential medium (MEM) and 10% calf serum medium. For tests $2.5 \times 10^5$ cells/ml from 3–5 day-old roller bottles were transferred to 60 mm tissue culture dishes at 5 ml/dish. After 24 hrs of incubation (37° C., 5% $CO_2$, high humidity), the cell layers were washed twice with 1X Hanks balanced salt solution (HBSS), using 2 ml/wash. Subsequently, an appropriate dilution of virus was applied in a 0.5 ml volume containing 200–400 plaque forming units (PFU) per ml. The virus was allowed to adsorb onto the cells for 1–2 hrs by gently rocking with an automatic rocker. The excess virus was removed and an agar overlay containing the desired dilution of the test material was applied to total 7 ml/dish. The agar was allowed to set at room temperature and then incubated (33°, 2.5% $CO_2$, high humidity). In about 6 days, when the plaques were well developed in control dishes, each dish was stained with 1% crystal violet. The efficacy of the treatment is computed by comparison with the number of plaques appearing in control dishes.

At concentrations of Justicidin P ranging from 64 µg/ml to 1 µg/ml, the compound demonstrated severe cytotoxicity, destroying the test cell layers. However, at lower concentrations Justicidin P isolated from natural sources demonstrated antiviral activity against both Herpes Type 1 and Type 2 virus. The extent of the plaque formation inhibition activity observed is set forth in the following Table 6. For purposes of comparison, acyclovir (9-(2-hydroxy-ethoxymethyl)guanine) under similar test conditions demonstrated 90% inhibition of Type 1 plaque formation at 8 µg/ml, and 90–99% inhibition of Type 2 in the range between 0.5 µg/ml and 8 µg/ml.

In a substantially similar series of tests in which IMR-90 cells were used, Justicidin P isolated from natural sources exhibited cytotoxicity at all concentrations tested. However, IMR-90 cells were also sensitive to acyclovir under substantially similar test conditions.

TABLE 6

Inhibition of Plaque Formation by Natural Justicidin-P in HeLa Cells Infected with HSV-1 and HSV-2

| Concentration ($\mu$g/ml) | Herpus Virus Type | Plaques/ Plate | Mean Plaques/ Plate | Inhibition (%) |
| --- | --- | --- | --- | --- |
| 0.25 | 1 | 87;86 | 87 | 31 |
| 0.063 | 1 | 128;116 | 122 | 2 |
| 0.016 | 1 | 114;120 | 117 | 6 |
| 0.004 | 1 | 141;126 | 134 | 0 |
| 0 (control) | 1 | 120;132 | 125 | — |
|  |  | 123 |  |  |
| 0.25 | 2 | 7;6 | 7 | 96 |
| 0.063 | 2 | 58;62 | 60 | 62 |
| 0.016 | 2 | 121;107 | 114 | 28 |
| 0.004 | 2 | 132;140 | 136 | 14 |
| 0 (control) | 2 | 185;141 | 158 | — |

Justicidin P analogues Nos. 17 (—O—n-propyl substituent at 3-position on lactone ring) and 18 (—SC$_7$H$_{15}$ substituent at 3-position) also demonstrated antiviral activity against Herpes Type 1 and Type 2 virus in HeLa cell layers. At a concentration of 1 $\mu$g/ml, compound 17 was cytotoxic, but at concentration of 0.1 $\mu$g/ml, compound 17 demonstrated an average of 71% plaque formation inhibition against Type 1, and an average of 91% inhibition against Type 2. Compound 18 was found to be cytotoxic at concentrations of 64 and 16 $\mu$g/ml, but demonstrated 81% inhibition against Type 1 at 4 $\mu$g/ml, and 17% inhibition against Type 1 at 1 $\mu$g/ml. Against Type 2, compound 18 exbibited 77% inhibition at 4 $\mu$g/ml, and 16% inhibition at 1 $\mu$g/ml. In this series of tests, compound 19 (—O—i-propyl substituent at 3-position) demonstrated cytotoxic properties at concentrations of 1, 4, 16 and 64 $\mu$g/ml.

Crude extracts of *J. extensa* and highly purified crystalline natural Justicidin P, prepared as described previously, were tested for antiviral activity against vesicular stomatitis virus (VSV) in human diploid fibroblast cells. The cells were grown in Eagle's minimum essential medium, supplemented with 7% fetal calf serum, at 37° C., 5% CO$_2$, and high humidity. The tests were conducted in microtiter plates. Each well received 40,000 cells from a 4 day-old culture and the plates were incubated for 18 hrs at 37° C.; then 1 plaque-forming unit (PFU) of VSV was added. The cells were incubated for 48 hrs at 37° C.; during this period the virus replicates and destroys the cells if they are not protected by the treatment. The effect was visualized by staining the cells with 1% crystal violet.

A series of dilutions of the test material was used in each experiment, to detect the lowest concentration which would protect cells against virus infection, and also, whether the compound exhibited cytotoxicity to cells free of virus. In this test, 50% protection against VSV is known to be provided by a known amount of human fibroblast interferon/ml and this activity is known as 1 unit. The activity of an unknown test material at a specific concentration thus could be computed on the unit basis.

The crude extract of *J. extensa* exhibited antiviral activity in the range of 2 to 20 $\mu$g/ml without detectable cytotoxicity. Highly purified crystalline natural Justicidin P was active in the 0.01 to 0.1 $\mu$g/ml range. There was some variation in the response from test to test, but an average of 1 unit activity was exhibited by 5 $\mu$g of the crystalline preparation. Qualitatively, cytotoxicity was observed at 10–60 fold higher levels.

Natural and synthetic Justicidin P, as well as a number of its synthetic analogues, were tested for antiviral activity against Human Rhino Virus (HRV-2) in a series of tests conducted in microtiter plates in a manner similar to that described for VSV, above. HeLa cells were routinely grown and maintained in cultures analogous to those described earlier. Each well of the microtiter plate received 4×10$^4$ cells in 200 $\mu$l volume, and the wells received varying amounts (100, 200 and 400 PFU) of HRV-2. The test materials were applied in a wide range of concentrations: 10, 2, 0.4, 0.08 and 0.016 $\mu$g/ml were tested by serial dilutions from a stock 5 mg/ml dimethyl sulfoxide solution. Following an appropriate incubation period (48 hrs), the cells were stained with 1% crystal violet and the protection against virus recorded by visual and photometric inspections. The efficacy of each compound was computed by comparing the optical densities of the controls and the treated wells. The cytotoxicity of the test compounds was also observed for identical concentrations in identical tests in which virus was omitted. In certain studies L cells were employed instead of HeLa cells. The results of the tests of Justicidin P and its synthetic analogues against HRV-2 are set forth in Table 7 below. The values reported represent the results of photometric comparisons with untreated controls.

TABLE 7

Inhibition of HRV-2 in HeLa Cells by Justicidin P and Synthetic Analogues (%)

| Compound | Substituent | PFU | % Inhibition by Test Compound at Test Concentration ($\mu$g/ml) | | | | |
| --- | --- | --- | --- | --- | --- | --- | --- |
|  |  |  | 10 | 2 | 0.4 | 0.08 | 0.016 |
| Justicidin P (natural) | —OCH$_3$ | 200 | 64 | ≥100 | ≥100 | ≥100 | 107 |
| Justicidin P (synthetic) | —OCH$_3$ | 400 | 43 | 73 | 0 | 0 | 0 |
| 14 | —F | 400 | 79 | 21 | 0 | 0 | 0 |
| 15 | —OOCCH$_3$ | 400 | 72 | 0 | 0 | 0 | 0 |
| 16 | —OH | 400 | 98 | 0 | 0 | 0 | 0 |
| 17 | —O—n-propyl | 200 | CT | ≥74 | ≥100 | ≥100 | ≥100 |
| 18 | —S—n-C$_7$H$_{15}$ | 200 | CT | CT | ≥100 | ≥100 | 80 |
| 19 | —O—i-propyl | 200 | CT | 14 | 107 | ≥100 | 100 |
| 20 | —O—n-C$_{12}$H$_{25}$ | 200 | 83 | 74 | 10 | 0 | 0 |
| acyclovir | — | 400 | 0 | 0 | 0 | 0 | 0 |

The notation "CT" indicates that the cell layer was destroyed, indicating cytotoxicity at this concentration.

Toxicity Studies

In vivo toxicity studies of natural and synthetic Justicidin P produced mixed results. In a series of studies in which natural Justicidin P was administered orally to out-bred mice at dosage levels up to about 324 mg/kg, no toxicity was observed. However, natural and synthetic Justicidin P were toxic to A/JAX inbred mice when administered orally at dosages of 200 and 100 mg/kg.

In vitro toxicity studies of natural Justicidin P were conducted using Madin-Darby Canine Kidney (MDCK) cells and test concentrations ranging between 0.01 and 0.56 μg/ml. In these tests, Justicidin P was suspended in MEM, diluted, and suspended in a purified agar solution. Duplicate plates containing MDCK cell layers were washed twice with HBSS, overlayed with the test compound-agar solutions, and incubated at 34° C., 5% $CO_2$ for 72 hours. At the conclusion of the incubation period, cell layers were stained with 1% crystal violet, rinsed with tap water, dried and visually inspected to determine toxicity. The results of these experiments are set forth in Table 8, below.

TABLE 8

Justicidin P Toxicity in MDCK Cells

| Compound Concentration (μg/ml) | % Toxicity |
| --- | --- |
| 0.56 | 70 |
| 0.25 | 40 |
| 0.11 | 30 |
| 0.05 | 15 |
| 0.02 | 5 |
| 0.01 | 1 |

The foregoing test data demonstrate the insecticidal and antiviral activity of the compounds of the invention. In particular, the antiviral effectiveness of the compounds of the invention, compared to acyclovir, is pronounced at extremely low concentrations. Moreover, the spectrum of antiviral activity exceeds that of acyclovir under the experimental conditions reported.

What is claimed is:

1. A compound having the formula

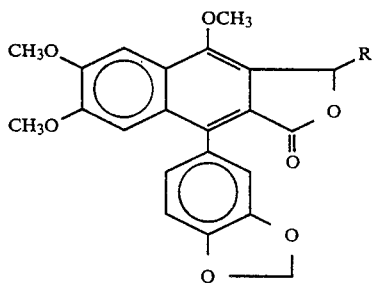

wherein
R is —F, —OOCCH$_3$, —OR$^1$, or —SR$^1$; where R$^1$ is —H or an alkyl group of 1 to 12 carbon atoms, provided that when R is —OCH$_3$, the compound is a synthetic product, or a purified component of a fraction or extract isolated from natural sources such as crude extracts of *Justicia extensa*.

2. A compound according to claim 1 wherein R is —F, —OOCCH$_3$, or —OR$^1$, where R$^1$ is an alkyl group of 1 to 5 carbon atoms.

3. The compound according to claim 2 wherein R is —F.

4. The compound according to claim 2 wherein R is —OOCCH$_3$.

5. The compound according to claim 2 wherein R is —OR$^1$ and R$^1$ is —CH$_3$.

6. The compound according to claim 2 wherein R is —OR$^1$ and R$^1$ is an —n—propyl group.

7. The compound according to claim 2 wherein R is —OR$^1$ and R$^1$ is an isopropyl group.

8. The compound according to claim 1 wherein R is —SR$^1$ and R$^1$ is —n—C$_7$H$_{15}$.

9. A composition for killing insects comprising a suitable carrier and an insecticidally effective amount of a compound of claim 2.

10. A composition for killing insects comprising a suitable carrier and an insecticidally effective amount of the compound of claim 3.

11. A composition for killing insects comprising a suitable carrier and an insecticidally effective amount of the compound of claim 4.

12. A composition for killing insects comprising a suitable carrier and an insecticidally effective amount of the compound of claim 5.

13. A composition for killing insects comprising a suitable carrier and an insecticidally effective amount of the compound of claim 6.

14. A composition for killing insects comprising a suitable carrier and an insecticidally effective amount of the compound of claim 7.

15. A composition for treatment of viral infection in mammals comprising a pharmaceutically suitable carrier and an effective antiviral amount of a compound of claim 1.

16. A composition for treatment of viral infection in mammals comprising a pharmaceutically suitable carrier and an effective antiviral amount of the compound of claim 5.

17. A composition for treatment of viral infection in mammals comprising a pharmaceutically suitable carrier and an effective antiviral amount of the compound of claim 6.

18. A composition for treatment of viral infection in mammals comprising a pharmaceutically suitable carrier and an effective antiviral amount of the compound of claim 7.

19. A composition for treatment of viral infection in mammals comprising a pharmaceutically suitable carrier and an effective antiviral amount of the compound of claim 8.

20. A method of killing insects comprising contacting insects with a composition of claim 9.

21. A method of killing insects comprising contacting insects with a composition of claim 10.

22. A method of killing insects comprising contacting insects with a composition of claim 11.

23. A method of killing insects comprising contacting insects with a composition of claim 12.

24. A method of killing insects comprising contacting insects with a composition of claim 13.

25. A method of killing insects comprising contacting insects with a composition of claim 14.

26. A method for treatment of viral infection in mammals comprising administering internally to a mammal a composition of claim 15.

27. A method for treatment of viral infection in mammals comprising administering internally to a mammal a composition of claim 16.

28. A method for treatment of viral infection in mammals comprising administering internally to a mammal a composition of claim 17.

29. A method for treatment of viral infection in mammals comprising administering internally to a mammal a composition of claim 18.

30. A method for treatment of viral infection in mammals comprising administering internally to a mammal a composition of claim 19.

* * * * *